US008765864B2

(12) United States Patent
Kierkels et al.

(10) Patent No.: US 8,765,864 B2
(45) Date of Patent: Jul. 1, 2014

(54) MELAMINE CYANURATE IN CRYSTALLINE FORM

(75) Inventors: Renier Henricus Maria Kierkels, Beegden (NL); Philippe Wolfgang Paul Valere Bleiman, Hasselt (BE); Leopold Franciscus Wynandus Vleugels, Beek (NL)

(73) Assignee: BASF SE, Ludwigshafen (DE)

( * ) Notice: Subject to any disclaimer, the term of this patent is extended or adjusted under 35 U.S.C. 154(b) by 1681 days.

(21) Appl. No.: 11/664,660

(22) PCT Filed: Oct. 6, 2005

(86) PCT No.: PCT/EP2005/055036
§ 371 (c)(1),
(2), (4) Date: Feb. 7, 2008

(87) PCT Pub. No.: WO2006/040289
PCT Pub. Date: Apr. 20, 2006

(65) Prior Publication Data
US 2008/0312360 A1 Dec. 18, 2008

(30) Foreign Application Priority Data
Oct. 15, 2004 (EP) .................................... 04105066

(51) Int. Cl.
*C08G 18/42* (2006.01)
*C08K 5/34* (2006.01)
*C08K 5/3492* (2006.01)
*C07D 251/70* (2006.01)
*C09K 21/10* (2006.01)
*C07D 251/54* (2006.01)

(52) U.S. Cl.
CPC .......... *C07D 251/54* (2013.01); *C08K 5/34928* (2013.01); *C07D 251/70* (2013.01); *C09K 21/10* (2013.01)
USPC .......................................... 524/500; 524/101

(58) Field of Classification Search
USPC ................ 162/164.1, 166, 168.2, 168.3, 206; 442/179, 180, 377; 524/101, 512, 143, 524/163, 418, 500; 544/192
See application file for complete search history.

(56) References Cited

U.S. PATENT DOCUMENTS

| 3,532,635 | A | | 10/1970 | Hans ............................. 252/152 |
| 5,202,438 | A | | 4/1993 | Paul ............................. 544/198 |
| 5,684,071 | A | * | 11/1997 | Mogami et al. ............... 524/100 |
| 6,521,682 | B1 | * | 2/2003 | Costantino et al. ........... 524/101 |

FOREIGN PATENT DOCUMENTS

| EP | 0601542 | | 6/1994 | |
| WO | WO 9306157 A1 | * | 4/1993 | ................. C08J 5/10 |
| WO | WO 03/035736 A | * | 5/2003 | ............... C08K 9/04 |

OTHER PUBLICATIONS

Patent Abstracts of Japan Publication No. 05310716, Nov. 22, 1993.
Patent Abstracts of Japan Publication No. 08157595, Jun. 18, 1996.
Patent Abstracts of Japan Publication No. 07149739, Jun. 13, 1995.
Patent Abstracts of Japan Publication No. 07188193, Jul. 25, 1995.
Patent Abstracts of Japan Publication No. 54055588, May 2, 1979.
Patent Abstracts of Japan Publication No. 56032470, Apr. 1, 1981.
Derwent Abstr. 95-082520/12 for DE 19503925, Jan. 1995.

* cited by examiner

*Primary Examiner* — Hui Chin
(74) *Attorney, Agent, or Firm* — Tyler A. Stevenson

(57) ABSTRACT

The present invention relates to a novel process for preparing solid, small particles comprising melamine cyanurate in essentially crystalline form. A concentrated aqueous dispersion is prepared of a mixture of cyanuric acid and melamine and selected surfactants are added to the dispersion.

7 Claims, No Drawings

MELAMINE CYANURATE IN CRYSTALLINE FORM

The present invention relates to a novel process for preparing solid, small particles comprising melamine cyanurate in essentially crystalline form, a flame retardant composition, a new crystal form (α-form) of melamine cyanurate, a process for preparing the new crystal form and a process for preparing a mixture of crystal forms (α-form and β-form) of melamine cyanurate.

Melamine cyanurate (MC) is the salt formed from melamine and cyanuric acid and is known for its use in polymers as a flame retardant. Flame retardants are added to polymeric materials (synthetic or natural) to enhance the flame retardant properties of the polymers. Depending on their composition, flame retardants may act in the solid, liquid or gas phase either chemically, e.g. as a spumescent by liberation of nitrogen, and/or physically, e.g. by producing a foam coverage. Flame retardants interfere during a particular stage of the combustion process, e.g. during heating, decomposition, ignition or flame spread. MC can be used alone or in combination with other flame-retardants, thus causing heat sink and dripping of the flame retarded material.

EP-A-439 719 discloses the use of nitrogen liberation agents, such as melamine cyanurate, as a flame retardant agent in polymers. The flame retardant agent is particularly effective when small powder particles are distributed homogeneously in the polymer matrix. MC powder is currently manufactured by separation from a concentrated aqueous suspension of melamine and cyanuric acid. Upon heating both compounds dissolve in the aqueous phase and MC, which is considerably less soluble in water [MC: 0.008 g/100 ml (20° C.) as compared with melamine: 0.3 g/100 ml (20° C.), 4.6 g/100 ml (95° C.) and cyanuric acid: 0.3 g/100 ml (20° C.), 2.5 g/100 ml (95° C.)] begins to crystallize. After completing the crystal formation, the solid particles are isolated, dried and milled to the requested particle size, e.g. 15, 25 or 50μ.

The use of small powder particles bears other risks, such as formation of dust, and safety problems from the risk of dust explosions, spark ignition from electrostatic potentials, segregation and separation processes, dosage problems resulting from an inadequate flow ability, or formation of aggregates.

There is a need for commercial dosage forms that avoid these disadvantages. According to EP-A-0 666 259 larger MC-agglomerates are formed of an average size of less than 100μ with metal oxide particles. These agglomerates disintegrate easily at elevated temperatures when formulated in the polymer matrix.

According to WO 03/035736 dust formation is reduced by producing free flowing MC-agglomerates that contain smaller MC-particles of an average size between 0.1 and 50μ which are bonded with each other with the aid of an auxiliary material, such as polyvinyl alcohol (PVA), polyvinyl pyrrolidone (PVP) or polyvinyl caprolactam.

The present invention relates to the problem of preparing solid, small particles comprising melamine cyanurate that avoid the risk of undesirable dust formation, as well as the separate step of forming agglomerates with auxiliary materials.

It has surprisingly been found that solid, small particles comprising melamine cyanurate in essentially crystalline form without additional agglomerates are obtained from a mixture of equimolar amounts of cyanuric acid dihydrate and melamine that contains less than 5% by weight of free (unbounded) water or by addition of a suitable surfactant to a mixture of solid, cyanuric acid and melamine.

The present invention relates to a process for preparing solid, small particles comprising melamine cyanurate in essentially crystalline form. The process is characterized by the following process embodiments:
a) A mixture of equimolar amounts of cyanuric acid dihydrate and melamine that contains less than 5% by weight of free water is prepared by converting cyanuric acid into its dihydrate, forming a mixture of the cyanuric acid dihydrate with melamine and heating that mixture to a temperature above 80° C.; or
b) A concentrated aqueous dispersion is prepared comprising at least 25 weight percent, based on the total weight of the dispersion, of a mixture of cyanuric acid and melamine and adding to that mixture an additive selected from the group consisting of
b') Diallyidialkylammonium chloride or a homopolymer or a copolymer thereof; and
b") A low molecular weight styrene/maleic anhydride copolymer or a partial ester derivative or hydrolysis product thereof; and
isolating the particles obtainable from the aqueous dispersion. The general terms used in the description of the instant invention, unless defined otherwise, are defined as follows:

The term solid particles defines any aggregates or agglomerates of solid particulate matter, such as powders, crystals, comminuted crystals or granulates prepared from crystals and the like.

The term small particles defines a distribution of particles obtainable by the process of the present invention, wherein a fraction of at least 90%, preferably 95%, has a particle diameter of less than 1μ and the remaining particles are not larger than 5μ.

The term "crystalline form" defines any solid matter, wherein the molecules are arranged in a geometrically regular pattern, as opposed to amorphous forms.

The term "in essentially crystalline form" defines the exclusion of substantial amounts of amorphous particles from any compositions or agglomerates of crystalline particles.

By means of analytical measurements from microscopic, laser light scattering or electron micrographs, the size and homogeneity of the solid particles obtained by the claimed process is determined.

According to a preferred embodiment of the invention an average particle size (D50) of less than 0,8μ for a population of ≥99% (D99)<5μ is observed.

Process Variant a)

For the preparation of the mixture of the cyanuric acid dihydrate with melamine a high speed mixer (Diosna) is used. The mixing in the reactor is effected at higher speeds, e.g. at a minimum of 500 rpm. Four bladed stainless steel mixing rotors are preferred. The exact amount of water for forming the dihydrate is added to the preheated (between 30-60° C.) anhydrous cyanuric acid over a time period of at least 30 minutes while mixing at least 500 rpm. A surplus of free water of up to 5%, based on the total weight of the mixture, is possible. After forming the dihydrate melamine is added at the same temperature, and the mixture is stirred for several hours.

The term "free water" defines the amount of water present in the mixture, which is not consumed by anhydrous cyanuric acid for the formation of hydrates, e.g. the dihydrate. Free or unbound water can be determined by regular analytical methods, e.g. the so-called Karl Fischer method or by drying at 120° C. for at least 2 hours.

The temperature range when mixing the cyanuric acid dihydrate with melamine is from about 80°-200° C., preferably 80°-120° C., particularly 90°-100° C.

The advantage of this process variant is seen in the fact that no removal of water by drying is necessary. A powdery product is obtained that does not have to be milled. The powdery product may be directly further processed to compressed articles, such as granulates.

According to another embodiment of the invention a new crystal modification (β-form) of melamine cyanurate is formed by process variant a) in the presence of up 5% free water, based on the total weight of the mixture. The new crystal form has a temperature of sublimation, as determined by DSC (Differential Scanning Calorimetry), of 424° C. and can be differentiated clearly from other crystal form, such as the α-crystal form, which is obtainable by other methods, such as the ones as described in JP 07149739-A (Nissan).

The new crystal modification (β-form) of melamine cyanurate is also distinguishable from mixtures, wherein both crystal forms, the α-form and the β-form, are present in varying amounts, depending on the chosen method for preparing the melamine cyanurate.

The following physico-chemical data, based on DSC and dynamic thermogravimetric analysis, have been established with regard to the α- and the β-crystal forms and mixtures thereof:

TABLE 1

| Crystal Form | $T_{subl}$ [° C.] | $\Delta H_{subl}$ [J/g] | $T_{start}$degr [° C.] | $(dm/dt)_{300}$ [%/° C.] | $(dm/dt)_{max}$ [%/° C.] |
|---|---|---|---|---|---|
| α-Form | 417 | 1530 | 252 | −1.3 | −41.2 |
| β-Form | 424 | 1730 | 272 | −0.5 | −37.0 |
| Mixture α-/β-Form | 420 | | 267 | −0.5 | −41.6 |

The β-form of melamine cyanurate is characterised in the X-ray powder diffraction pattern by the interplanar spacings [d-values] and relative line intensities of the following principal lines intensities including, medium lines and weaker lines (CuKα radiation:40 KV, 50 mA, monochromator in the diffracted beam, receiving slit: 0.2 mm, scatter slit 1°):

TABLE 2

β-Form

| d-Spacing [$10^{-10}$ m] | Relative Intensity [%] |
|---|---|
| 8.250 | 48 |
| 4.790 | 4 |
| 4.120 | 9 |
| 4.000 | 8 |
| 3.190 | 100 |
| 2.759 | 5 |
| 2.681 | 6 |
| 2.414 | 4 |
| 2.289 | 5 |
| 1.814 | 4 |
| 1.659 | 3 |
| 1.599 | 4 |

Another embodiment of the invention relates to the process for preparing the crystal form (β-form) of melamine cyanurate. This process is characterised in that a mixture of equimolar amounts of cyanuric acid dihydrate and melamine that contains less than 5% by weight of free water is prepared by converting cyanuric acid into its dihydrate, forming a mixture of the cyanuric acid dihydrate with melamine and heating that mixture to a temperature above 80° C.

The new crystal form (β-form) is advantageous as compared with other crystal forms. It is particularly useful in the process described above for preparing solid, small particles comprising melamine cyanurate in essentially crystalline form, as it assures a rapid and complete crystallization process and assure superior mechanical properties, such as a good storage stability or flow ability, of the crystals themselves or further processed solid dosage forms, such as granulates.

According to another embodiment of the invention a new crystal modification (β-form) of melamine cyanurate is formed by process variant a) in the presence of up 5% free water, based on the total weight of the mixture. The new crystal form has a temperature of sublimation, as determined by DSC (Differential Scanning Calorimetry), of 424° C. and can be differentiated clearly from other crystal form, such as the α-crystal form, which is obtainable by other methods, such as the ones as described in JP 07149739-A.

The new crystal modification (β-form) of melamine cyanurate is also distinguishable from mixtures, wherein both crystal forms, the α-form and the β-form, are present in varying amounts, depending on the chosen method for preparing the melamine cyanurate.

Process Variant b)

The term aqueous dispersion comprises any mixture of two phases wherein dispersed particles are distributed homogeneously in a dispersant phase (dispergens), which in the instant case is water. The aqueous phase may contain other substances like solutes (soluble salts), acids or bases, sequestering agents or dispersing agents and/or surface active compounds that may assist in stability the dispersion.

The term aqueous dispersion is defined within the limits of so-called solid/liquid or liquid/liquid disperse systems, e.g. emulsion, dispersion, as opposed to other types of dispersions, such as solid/gas, e.g. fumes, or gas/liquid, e.g. foams, dispersions. Solid/liquid dispersions that apply here consist of two-phase systems containing insoluble solid particles or solid particles of low solubility within a liquid. Liquid/liquid dispersions are commonly defined as emulsions and consist of two separate phases of different polarity. In the instant case a non-polar phase is dispersed in the polar phase, which is water.

The term dispersed particles comprises solid and, in particular, liquid particles, in the instant case the compound of the formula (I), to be distributed homogeneously within a liquid phase, e.g. water. Homogeneous distribution means that the concentration of the solid or liquid particles within the liquid dispersion agent is identical or approximately identical in any volume fraction of that liquid phase (even distribution of liquid or solid particles).

The amount of cyanuric acid and melamine to be dispersed may vary within wide limits to give a concentration between about 10.0 to 90.0%, particularly 10 to 72%, preferably 40.0 to 72%, and most preferably 50.0 to 72.0% (by weight). Water is present in the dispersion as the remainder to make 100.0% by weight. The addition of purified, e.g. deionised or distilled, water is preferred.

Dialkyldiallylammonium chlorides are known compounds, classified in the group of cationic surfactants, and are commercially available. According to a preferred embodiment of the process, diallyldimethylammonium chloride [CAS Reg. No. 7398-69-8] or a homopolymer or copolymer thereof is added to the suspension. This cationic surfactant is available from Ciba Specialty Chemicals: CIBA Ageflex®mDADMAC.

The cationic homopolymer or copolymer of dialkyldiallylammonium chlorides according to process variant b') are known compounds and are commercially available from Floerger S. A.: Posifloc®, e.g. the product POSIFLOC CL45VHM (high molecular weight polydiallyldimethylammonium chloride) or POSIFLOC CL45 (low molecular weight polydiallyidimethylammonium chloride).

Cationic homopolymer or copolymer of dialkyldiallylammonium chlorides can be produced by free-radical polymerisation, cf. the entry *Flocculants in Ullmann's Encyclopedia of Industrial Chemistry, Wiley-VCH Verlag* (2002 on-line edition) by H. Burkert and J. Hartman in *Ullmann's Encyclopaedia of Industrial Chemistry, Wiley-VCH Verlag* (2002 Online edition).

The low molecular weight styrene/maleic anhydride copolymer or a partial ester derivative or a hydrolysis product thereof b") are known polymers, cf. the entry *Polystyrene and Styrene Copolymers* by B. G. Frushour and J. R. Kontoff in *Ullmann's Encyclopaedia of Industrial Chemistry, Wiley-VCH Verlag* (2002 On-line edition). The copolymers are obtainable by polymerisation of styrene with maleic anhydride. The partial esters can be produced by esterification of the copolymer with an alcohol. The hydrolysis products are obtainable by reaction of the low molecular weight styrene/maleic anhydride copolymer or the partial ester derivative thereof with an aqueous base.

The low molecular weight styrene/maleic anhydride copolymer or the partial ester derivative or hydrolysis product thereof are commercially available from Elf Atochem: SMA®, cf. the products SMA 1000, 2000, 3000 EF 30, EF 40 (low molecular weight styrene/maleic anhydride copolymers), SMA 1440, 17352, 2625, 3840 (low molecular weight styrene/maleic anhydride copolymer partial ester derivatives), SMA 1000 H/HNa, 2000 H/HNa, 3000 H/HNa, 4000 H/Na (low molecular weight styrene/maleic anhydride copolymer hydrolysis products), SMA 1440 H, 1440 HDN, 2625H, 17352 HD (hydrolysis product of low molecular weight styrene/maleic anhydride copolymer partial ester derivatives).

The above-mentioned additives are present in the aqueous dispersion in an amount from 0.1 to 10.0% (by weight), preferably 0.1 to 5.0%, most preferably 0.5 to 1.0%, based on the total weight of the dispersed phase.

A preferred embodiment of the invention relates to process variant b), wherein an additive selected from the group consisting of
  b') Dimethyldiallylammonium chloride or a homopolymer thereof; and
  b") A low molecular weight styrene/maleic anhydride
is added to the concentrated aqueous dispersion comprising a mixture of cyanuric acid and melamine.

In a preferred embodiment of the invention the aqueous dispersion is made basic by the addition of suitable bases, such as diluted sodium or potassium hydroxide, ammonia or amines, such as dimethylethylamine. The base is present in amount from about 0.5 to 2.0%, preferably about 0.5 to 2.0%, based on the weight of the dispersion.

The dispersion is made homogeneous by conventional mixing methods, such as the ones known for preparing emulsions or suspensions. Mixing is effected thoroughly throughout the dispersion by vigorous shaking using a dispersing machine, for example a Vortex mixer, or using dispersing machines of the ®POLYTRON type (Kinematica AG, Littau Switzerland) or dispersing machines produced by IKA (Staufen Germany), a static mixer and conventional stirring machines having a propeller, anchor or paddle blade or using a phase mixer.

In order to obtain an especially homogeneous mixture, stirring is carried out at high speed, for example using Y-beam agitators (®Y-Strahl, ®Ultraturrax) or stirring machines produced by Polytron, for example Polytron PT 3000 or DH 30/30, or using a high pressure rotor/stator mixer, for example the BUSS mixing turbine.

According to an optional embodiment of the process, subsequent crystallisation of solid particles is carried out, if desired, by inoculating the emulsion with suitable crystal seeds, e.g. melamine or anhydrous cyanuric acid.

The time period needed for forming the solid, small particles may vary within wide limits and depends on a batchwise or continuous process procedure. In a batch process a suitable time period is from 1-30 minutes.

The solid particles formed by the process are almost 100% crystalline and virtually free of amorphous particles. Crystalline isolates, such as granulates, meet stringent quality requirements with regard to light stability.

A further embodiment of the invention relates to the aqueous dispersion comprising at least 25 weight percent, based on the total weight of the dispersion, of a mixture of cyanuric acid and melamine and an additive selected from the group consisting of
  b') Diallyidialkylammonium chloride or a homopolymer or a copolymer thereof; and
  b") A low molecular weight styrene/maleic anhydride copolymer or a partial ester derivative or hydrolysis product thereof.

The solid particles present in the aqueous dispersion are subsequently separated from the aqueous dispersion and may be subsequently dried, and, if desired, converted to smaller particles sizes by conventional grinding methods, such as wet grinding with a ball mill. This prevents the inclusion of air or other undesirable particles.

The separation from the aqueous dispersion includes the application of any state of the art method known for separating binary solid/liquid mixtures, e.g. filtration, centrifugation or decantation. To remove any impurity the crystalline residue may be purified by the addition of water and subsequently dried by applying the known drying techniques, particularly by applying reduced pressure or a vacuum at elevated temperatures up to 100° C.

A further embodiment of the invention relates to a process, which essentially consists of a combination of process variants a) and b). A mixture of equimolar amounts of cyanuric acid dihydrate and melamine that contains less than 5% by weight of free water is prepared by converting cyanuric acid into its dihydrate, forming a mixture of the cyanuric acid dihydrate with melamine and heating that mixture to a temperature above 80° C. An aqueous dispersion comprising the additive selected from the group consisting of diallyidialkylammonium chloride or a homopolymer or a copolymer thereof and a low molecular weight styrene/maleic anhydride copolymer or a partial ester derivative or hydrolysis product thereof is added and the mixture is subjected to high shear mixing.

A further embodiment of the invention relates to the subsequent process step of further processing to other solid particle forms the solid, small particles obtained by performing either one of process variant a) or b).

According to a preferred embodiment of that process the crystals obtained are separated from the dispersion and converted to granulates.

The term solid particles also defines further processed compressed particle forms, to which pressure has been applied when forming the particles from solid aggregates or agglomerates.

The compressed particles, such as granulates, comprising solid, small particles comprising melamine cyanurate in essentially crystalline form, obtainable by the process as defined above, are also subject matter of the present invention.

Compressed particle forms are obtained by applying conventional machinery, such as internal mixers, extruders, e.g. single or twin screw extruders or planetary roller extruders, or kneaders. If an internal mixer or extruder is employed, the process is preferably carried out continuously, whereas in a kneader the process is preferably carried out batch-wise. The dried comprimates obtained, e.g. the extrudates, may then be reduced to the desired particle sizes by applying conventional grinding or milling techniques.

The term compressed particle forms particularly relates to further processed granulates formed from powders or any other fine particles by applying conventional granulation methods, such as wet granulation or compaction.

Many methods are known for the manufacture of granules and related agglomerates. Granules may be formed from powders and other fine particles by suitable agitation in the presence of a suitable binding liquid, such as water. Granules may also be formed from powders by pressurized compaction and extrusion methods by applying pressure. Application of heat to the powder may result in the sintering and formation of agglomerates of suitable size. Drying and solidification on surfaces may also produce granular products. Solutions, suspensions or melts are applied to a heated or cooled surface, and the solids are scraped off. In spray-drying, a pumpable and dispersible feed liquid, which may be a solution, gel, paste, emulsion, slurry or melt, is sprayed into a chamber, wherein solidification occurs. The chamber is heated to evaporate the solubilising or emulsifying liquid, or cooled down to allow the solidification of a melt.

The solid particle forms, or, in the alternative, the aqueous dispersion from which the solid particle forms are prepared, or the compressed particle forms defined above optionally comprise additional additives, so-called blends, suitable for use in polymers, preferably additives customarily used for improving the chemical and physical properties of polymers containing these additives. The auxiliaries can be present in varying proportions, for example, in amounts of up to 40.0% by weight, preferably from 0.05% to 40.0% by weight, more preferably from 0.05% to 25.0% by weight, with particular preference from 0.05% to 10.0% by weight, based on the total weight of the composition.

A further embodiment of the invention relates to a mixture of different crystal modifications (α-form and β-form) of melamine cyanurate obtainable by process variant b)). The components of this mixture are characterised in the X-ray powder diffraction pattern by the following interplanar spacings [d-values] and relative line intensities including the principal lines, medium lines and weaker lines (CuKα radiation: 40 KV, 50 mA, monochromator in the diffracted beam, receiving slit: 0.2 mm, scatter slit 1°), which are characteristic for each crystal form present in the mixture:

TABLE 3

| α-Form | |
| --- | --- |
| d-Spacing [$10^{-10}$ m] | Relative Intensity [%] |
| 8.080 | 100 |
| 7.410 | 61 |
| 4.820 | 3 |
| 4.400 | 4 |
| 4.040 | 27 |
| 3.709 | 13 |
| 3.578 | 3 |
| 3.260 | 17 |
| 3.173 | 100 |
| 2.941 | 3 |
| 2.873 | 9 |
| 2.831 | 5 |
| 2.695 | 15 |
| 2.628 | 6 |
| 2.526 | 3 |
| 2.473 | 6 |
| 2.416 | 2 |
| 2.371 | 7 |
| 2.292 | 5 |
| 2.267 | 3 |
| 2.237 | 2 |
| 2.206 | 3 |
| 2.178 | 5 |
| 2.131 | 1 |
| 2.072 | 3 |
| 1.998 | 2 |
| 1.919 | 1 |
| 1.841 | 2 |
| 1.823 | 4 |
| 1.797 | 3 |
| 1.776 | 3 |
| 1.743 | 2 |
| 1.726 | 2 |
| 1.690 | 2 |
| 1.676 | 2 |
| 1.639 | 2 |
| 1.623 | 4 |
| 1.587 | 3 |
| 1.570 | 1 |

The interplanar spacings [d-values] and relative line intensities, including the principal lines, medium lines and weaker lines, which are characteristic for the α-form are listed in Table 2 above.

A further embodiment of the invention relates to a process for preparing a mixture of crystal forms (α-form and β-form) of melamine cyanurate. The process is characterized in that a concentrated aqueous dispersion is prepared comprising at least 50 weight percent, based on the total weight of the dispersion, of a mixture of cyanuric acid and melamine and adding to that mixture an additive selected from the group consisting of b') Diallyldialkylammonium chloride or a homopolymer or a copolymer thereof; and b") A low molecular weight styrene/maleic anhydride copolymer or a partial ester derivative or hydrolysis product thereof; and isolating the solid particles obtainable from the aqueous dispersion.

The mixture of crystal forms (α-form and β-form) of melamine cyanurate, as obtained by the process described above, is also subject matter of the present invention.

The solid, small particles comprising melamine cyanurate in essentially crystalline form are characterized by their superior application properties, such as a good storage stability or flow ability. This applies to the crystals themselves or further processed solid dosage forms, such as granulates. A particular advantage of these further processed solid dosage forms is the fact that they retain their free-flowing properties during handling and storage. As a result, the solid dosage forms can be incorporated within a polymer matrix in a highly constant dose. Therefore, a particularly homogeneous distribution of MC in the polymer is achieved.

Poor dosage applicability of melamine cyanurate may result in concentration fluctuations in the polymer. This effect is caused by a lack of homogeneity of the compositions obtainable from production. Poor dosage applicability of melamine cyanurate affects the reproducibility of the production process, for example the compounding process.

A constant concentration of the solid, small melamine cyanurate particles obtained by the process according to the invention in a polymer results not only in a constant composition in one individual polymer batch, but also in the virtual absence of fluctuations in composition among the various production batches. As a result, final processors, for example injection moulders, may process these polymers without any need to adjust the equipment within one batch or subsequent batches.

The flow properties are determined using the vessel method of Klein as described in Klein; Seifen, Öle, Fette, Wachse, 94, 849 (1968). This is a method that uses a series of outflow vessels wherein each one has a different opening in the bottom. The material to be tested is added to the vessel and the outflow from the opening in the bottom of the vessel is determined. The qualification of the flow properties is determined by the smallest opening through which the powder can still flow. The material with the best flow properties has the lowest qualification, i.e. 1 (see Table 1). Materials in the classes numbered 1-4 are usually called free flowing.

The agglomerates according to the invention have a flow value according to the Klein test, to be defined hereinafter, of lower than 4, preferably equal to or lower than No. 3. Most preferred are agglomerates with a flow value equal to or lower than No. 2. This assures good dosing properties to be achieved under virtually all relevant process conditions. A free flowing agglomerate is understood to be an agglomerate with a flow behaviour lower than number 4 on the Klein scale.

The incorporation of the solid, small particles comprising melamine cyanurate in essentially crystalline form into the polymer materials can be carried out, for example, by mixing in the particles and, if desired, further additives in accordance with known methods. The incorporation into the polymeric material may take place prior to or during the shaping operation or by applying the particles to the polymer.

The invention therefore relates in particular to compositions, wherein the solid, small particles comprising melamine cyanurate in essentially crystalline form dispersion is incorporated into and/or chemically linked with an elastomer/polymer.

A further embodiment of the invention relates to a flame retardant composition comprising
A) Solid, small particles as obtained by the process as described above; and
B) A mouldable polymer.

The solid, small particles dispersion defined above can be incorporated into polymers by the following methods:
As emulsion or dispersion (e.g. to lattices or emulsion polymers)
As a dry mix during the mixing in of additional components or polymer mixtures
By direct addition to the processing apparatus (e.g. extruder, internal mixer, etc.)
As a solution or melt.

The polymer compositions can be employed in various forms and processed to give various products, for example to films, fibres, tapes, moulding compounds or profiles, or as binders for coating materials, adhesives or putties.

The following Examples illustrate the invention:

Example 1

63,0 kg melamine and 64,5 kg cyanuric acid, which have been milled to an average particle size of 110μ, are added in equimolar amounts to a DRAIS reactor. The mixture is heated with stirring to 75° C. An additive dispersion containing 1% SMA 1000 (Elf Atofina), which has been made basic by the addition of 1% KOH, is added in an amount to produce a slurry of 55% by weight of solids content. The reaction mixture is stirred for 120 min, and the slurry obtained is dried by spray drying at 140° C.

The small particles obtained are characterized by a particle size distribution, wherein 95% of a selection has a particle diameter of less than 1μ and the remaining particles are not larger than 5μ (light-scattering Coulter LS-230 particle sizer).

Example 2

In a manner analogous to Ex. 1, an additive dispersion containing 1% POSIFLOC®CL45 PolyDADMAC (=polydiallylmethylammonium chloride) or POSIFLOC®CL45 (low molecular weight, obtainable from Floerger S. A.) is added. Small MC particles of a similar particle size distribution are obtained.

Example 3

64.5 kg cyanuric acid, which has been milled to an average particles size of 100μ, are added in equimolar amounts to a DIOSNA high speed mixer. 18.0 kg water is added to form the dihydrate of cyanuric acid. The mixture is stirred at room temperature for a time period of 15-30 min. to allow the formation of the dihydrate, which is obtained in the form of a dry powder. The equimolar amount of 63.0 kg melamine, which has been milled to an average particle size of 110μ, is added. The mixture is heated to about 100° C. and vigorously stirred with an ®Ultraturrax (IKA) mixer. After 4 h the temperature is increased further until the melamine cyanurate obtained is sufficiently dried. The product is subsequently removed from the reactor. The small particles obtained are characterized by a particle size distribution, wherein 95% of a selection has a particle diameter of less than 1μ, and the remaining particles are not larger than 5μ (light scattering Coulter LS-230 particle sizer).

Example 4

In a manner analogous to Ex. 3, equimolar amounts of cyanuric acid dihydrate and melamine are mixed with 5,1 kg water. The components are mixed for 10-60 seconds in a twin screw extruder. Small MC particles of a similar particle size distribution are obtained by extrusion.

Example 5

In a 250 ml glass beaker equipped with a magnet stirrer and an electrical heater 83.6 g SMA 1000 P, obtainable from Cray Valley, are added with stirring to 54.7 g potassium hydroxide (85%) solution obtainable from Merck and diluted with 334.5 g water. The solution is heated to 50-60° C. and stirred until it becomes clear. Evolution of heat resulting from an exothermal reaction is observed. 620 g cyanuric acid (1-1440) obtainable in big lumps from Nissan are loaded into a 1.5 l one-shaft kneader (LIST DTB 1.5) equipped with a reflux cooler and heating. The lumps are crushed in the kneader within 10 minutes. 605.8 g Melamine obtainable from DSM are added with stirring. The reaction mass is heated to 95° C. up to a maximum jacket temperature of 120° C. As soon as a temperature of 95° C. is reached, a mixture of 47.3 g of the K-SMA solution described above, diluted with 138.1 g water, is added within 1 hour. This amounts to a concentration of 1%

K-SMA in respect to melamine cyanurate. After the feed, the reaction mass is kept at reflux with a jacket temperature of 120° C. during 4 hours. The reflux cooler is then replaced with a descending cooler and a receiver connected to a vacuum pump. The jacket temperature is increased to 150° C., and the vacuum reduced slowly to 20-30 mbar. As soon as a temperature of 120° C. in the kneader is reached, the drying process is finished. The reaction mass is unloaded and analyzed. 1231.6 g product corresponding to 99.5% yield is obtained. The product is white, not dusty and free flowing. No crusts are observed in the kneader, the stirrer and or the inspection window.

The conversion is analyzed by thermogravimetrical analysis (TGA), in which free melamine and cyanuric acid can be detected by weight loss between 200° and 245° C. The heating rate of the TGA equipment is 3° C. per minute. The content of melamine and cyanuric acid is 0%. The purity of the melamine cyanurate is 98.8%. The particle size is determined in a 1% suspension in water by a Sympatex Helos (H0017) equipment. Ultrasonic radiation is applied for 3 minutes before the measurement. 90% of the particles have a diameter of less than 5.9 micron and 99% of the particles a diameter below 32.2 microns. Fine particles of melamine cyanurate can be produced even with unmilled starting materials at moderate temperatures and at high concentrations by using K-SMA as additive. The potassium content of the product amounted to 0.32%.

Example 6

Analogous to Example 3 the amount of 620 g of cyanuric acid is crushed in a kneader and mixed with 605.8 g melamine. After heating to 95° C., 23.6 g of the K-SMA solution described in Example 5 is diluted with 138.1 g water and fed within one hour to the reaction mass under stirring. The solids content in the reaction mass after adding the feed amounts to 87.0%, and the content of K-SMA in respect to the solid content in the reaction mass is 0.5%. The reaction mass is kept at 98-100° C. with stirring for another 5 hours. The reaction mass is dried at 120° C. and 30 mbar, cooled to 80° C., unloaded and analyzed. The unloaded product has a weight of 1229.3 g which corresponds to 99.8% yield. The product purity is 99.4% and no free cyanuric acid and melamine is detectable by TGA. Analysis of particle size distribution measured with the same method as in Example 5 shows that 90% of the particles have a diameter smaller than 18.1 microns and 99% less than 37.3 microns.

The invention claimed is:

1. An aqueous dispersion consisting essentially of
   at least 25 weight percent, based on the total weight of the dispersion, of a mixture of cyanuric acid and melamine,
   an additive selected from the group consisting of
      b') dimethyldiallylammonium chloride or a homopolymer or a copolymer thereof; and
      b") a low molecular weight styrene/maleic anhydride copolymer or a partial ester derivative or hydrolysis product thereof,
   a base and
   water.

2. A process for preparing solid, small particles comprising melamine cyanurate in essentially crystalline form,
   wherein a concentrated aqueous dispersion is prepared and the crystalline melamine cyanurate particles obtained from the concentrated aqueous dispersion are isolated,
   wherein the concentrated aqueous dispersion consists essentially of
   at least 25 weight percent, based on the total weight of the dispersion, of a mixture of cyanuric acid and melamine,
   an additive selected from the group consisting of
      b') dimethyldiallylammonium chloride or a homopolymer or a copolymer thereof; and
      b") a low molecular weight styrene/maleic anhydride copolymer or a partial ester derivative or hydrolysis product thereof,
   a base and
   water.

3. A process according to claim 2, characterized in that the solid, small particles obtained are further processed to other solid particle forms.

4. A process according to claim 3, characterized in that the solid, small particles are further processed to granulates.

5. A process according to claim 2, wherein components b') and b") are
   b') dimethyldiallylammonium chloride or a homopolymer thereof; and
   b") a low molecular weight styrene/maleic anhydride copolymer.

6. A process according to claim 2 where in the concentrated aqueous dispersion,
   b') dimethyldiallylammonium chloride or a homopolymer or a copolymer thereof is present.

7. A process according to claim 2 where in the concentrated aqueous dispersion,
   b") a low molecular weight styrene/maleic anhydride copolymer or a partial ester derivative or hydrolysis product thereof, is present.

* * * * *